United States Patent
Wolf et al.

(10) Patent No.: US 10,266,469 B2
(45) Date of Patent: Apr. 23, 2019

(54) PROCESS FOR PREPARING TERPINENE-4-OL

(71) Applicant: BASF Agro B.V., Arnhem (NL)

(72) Inventors: Bernd Wolf, Niederkirchen (DE); Michael Rack, Eppelheim (DE); Stefan Benson, Bensheim (DE); Roland Goetz, Neulussheim (DE); Helmut Kraus, Research Triangle Park, NC (US)

(73) Assignee: BASF Agro B.V., Arnhem (NL)

( * ) Notice: Subject to any disclaimer, the term of this patent is extended or adjusted under 35 U.S.C. 154(b) by 0 days.

(21) Appl. No.: 16/079,155

(22) PCT Filed: Feb. 16, 2017

(86) PCT No.: PCT/EP2017/053467
§ 371 (c)(1),
(2) Date: Aug. 23, 2018

(87) PCT Pub. No.: WO2017/144336
PCT Pub. Date: Aug. 31, 2017

(65) Prior Publication Data
US 2019/0071377 A1    Mar. 7, 2019

(30) Foreign Application Priority Data
Feb. 26, 2016    (EP) ................................. 16157541

(51) Int. Cl.
*C07C 35/18*    (2006.01)
*C07C 29/17*    (2006.01)
*C07D 303/04*    (2006.01)
*C07C 35/00*    (2006.01)

(52) U.S. Cl.
CPC .............. *C07C 29/17* (2013.01); *C07C 35/00* (2013.01); *C07C 35/18* (2013.01); *C07C 2601/16* (2017.05)

(58) Field of Classification Search
CPC ......... C07C 35/00; C07C 35/18; C07C 29/17; C07C 2601/16; C07D 303/00; C07D 303/04
See application file for complete search history.

(56) References Cited

U.S. PATENT DOCUMENTS 3,676,504 A * 7/1972 Leffingwell ............. C07C 35/18
568/825

FOREIGN PATENT DOCUMENTS

| | | |
|---|---|---|
| CN | 1467029 | 1/2004 |
| JP | H0248541 | 2/1990 |

OTHER PUBLICATIONS

International Search Report, issued in PCT/EP2017/053467, dated May 2, 2017.

* cited by examiner

*Primary Examiner* — Jafar F Parsa
(74) *Attorney, Agent, or Firm* — Brinks Gilson & Lione

(57) ABSTRACT

The present invention relates to a process for preparing terpinene-4-ol from limonene-4-ol via a hydrogenation reaction in the presence of a nickel catalyst.

13 Claims, No Drawings

PROCESS FOR PREPARING TERPINENE-4-OL

This application is a National Stage application of International Application No. PCT/EP2017/053467, filed Feb. 16, 2017. This application also claims priority under 35 U.S.C. § 119 to European Patent Application No. 16157541.0, filed Feb. 26, 2016.

DESCRIPTION

The present invention relates to a process for preparing terpinene-4-ol of the formula (II) from limonene-4-ol of the formula (I) via a hydrogenation reaction in the presence of a nickel catalyst.

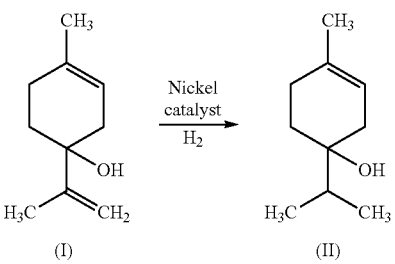

Terpinene-4-ol (also referred to as "1-isopropyl-4-methyl-cyclohex-3-en-1-ol" or "p-mentha-1-en-4-ol") is a monoterpene alcohol which is found in natural essential oils of many plants. This compound finds use in industrial applications as synthetic perfume and flavoring agent or intermediate thereof.

Because of the high costs and uncertainty of supply of the natural products, various synthetic routes to terpinene-4-ol have been developed.

JPH0248541 (A) describes a process for the production of the terpene alcohols limonene-4-ol and/or terpinene-4-ol from terpinolene-4,8-epoxide via an isomerization and/or hydrogenation reaction using a copper catalyst. As suitable reaction solvents, aromatic hydrocarbons, alicyclic hydrocarbons, saturated lower alcohols and glycols are mentioned. Specific reactions as recited in the examples were performed in ethanol, cyclohexane or 1,4-butanediol as solvent. In case terpinolene-4,8-epoxide is subjected to relatively low hydrogen pressures, limonene-4-ol is primarily generated. However, in order to obtain primarily terpinene-4-ol, relatively high hydrogen pressures are required, e.g. by increasing the hydrogen pressure towards the end of the reaction. Reactors suitable for high-pressure reactions are very expensive and require a high level of safety during operation. Besides, the reaction of limonene-4-ol conducted at higher pressures generates relatively high amounts of by-products (e.g. isopropyl-methyl-cyclohexenes and p-cymene) which reduce the yield and purity of the desired terpinene-4-ol.

U.S. Pat. No. 3,676,504 describes the hydrogenation of limonene-4-ol to terpinene-4-ol in the presence of Raney nickel as catalyst and ethanol as solvent. The hydrogenation reaction can be performed at a relatively low hydrogen pressure and temperature providing terpinene-4-ol in relatively high purity and good yield.

Nevertheless, there still remains room for improved or alternative routes for the hydrogenation of limonene-4-ol (I) to terpinene-4-ol (II) which is suitable for industrial scale-up.

It is therefore an object of the present invention to provide an improved or alternative process for the catalytic hydrogenation of limonene-4-ol (I) to terpinene-4-ol (II) which provides terpinene-4-ol (II) in high purity and yield and can be performed in a simple and economical manner and on an industrial scale.

These and further objects are in part or in whole achieved by a process for preparing terpinene-4-ol of formula (II)

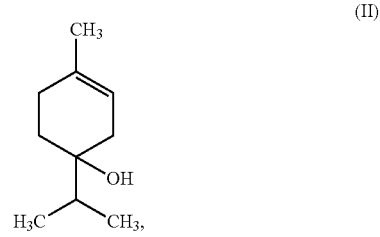

said process comprising contacting limonene-4-ol of formula (I)

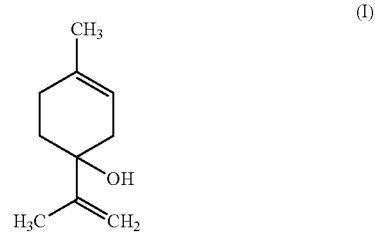

with hydrogen in the presence of at least one nickel catalyst and at least one inert organic solvent selected from carboxylic acid esters.

Accordingly, the aforementioned process for preparing terpinene-4-ol (II) is a subject matter of the present invention.

It has now surprisingly been found that the nickel-catalyzed hydrogenation of limonene-4-ol (I) to terpinene-4-ol (II) can be conducted in carboxylic acid esters as solvent while giving the desired terpinene-4-ol (II) in high purity and yield. This finding is all the more surprising and unexpected because it is known that carboxylic acid esters such as, for example, ethyl acetate, tend to undergo hydrolysis under the conditions of a nickel-catalyzed hydrogenation. Another advantage of the process according to the present invention is that it is possible to use a limonene-4-ol solution in the same carboxylic acid ester from a previous synthesis step without further purification or with only minor purification. Consequently, it is not necessary to use pure limonene-4-ol (I) as the starting material in the process of this invention. Thus, no tedious distillation procedures are required to separate limonene-4-ol (I) from the reaction mixture of the previous synthesis step. In addition, there is no need to replace the solvent used in the previous synthesis step so as to avoid additional thermal stress imposed on the product.

Thus, the present invention also relates to the use of a carboxylic acid ester (preferably any one of the preferred carboxylic acid esters as described herein, in particular ethyl acetate) as a solvent for the nickel-catalyzed hydrogenation of limonene-4-ol of formula (I), in particular in the presence of Raney nickel.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

Limonene-4-ol (also referred to as "1-Isopropenyl-4-methyl-cyclohex-3-en-1-ol" or "p-mentha-1,8-diene-4-ol") of the formula (I) used as a starting material in the process of this invention is a known compound that is commercially available or can be prepared in a known manner, for example, as described in U.S. Pat. No. 3,676,504, GB 1 307 053 and JPH0248541 (A).

Preferably, limonene-4-ol of formula (I) is prepared by isomerization of terpinolene epoxide of the formula (III)

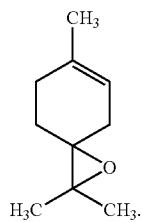

Terpinolene epoxide of the formula (III) is a known compound that is commercially available or can be prepared in a known manner, for example, as described in U.S. Pat. No. 3,676,504.

In another embodiment, the terpinolene epoxide of the formula (III) is further subjected to hydrogenation. Thus, limonene-4-ol (I) may be prepared by subjecting terpinolene epoxide of the formula (III) to isomerization and/or hydrogenation. In a preferred embodiment, the isomerization and/or hydrogenation of the terpinolene epoxide of the formula (III) is/are carried out in the presence of at least one copper catalyst, preferably at least one copper chromite catalyst. In another preferred embodiment, the isomerization and/or hydrogenation of the terpinolene epoxide of the formula (III) is/are carried out in the presence of the at least one inert organic solvent selected from carboxylic acid esters (preferably any one of the preferred carboxylic acid esters as described herein, in particular ethyl acetate). More preferably, the isomerization and/or hydrogenation of the terpinolene epoxide of the formula (III) is/are carried out in the presence of at least one copper catalyst (preferably at least one copper chromite catalyst) and at least one inert organic solvent selected from carboxylic acid esters (preferably any one of the preferred carboxylic acid esters as described herein, in particular ethyl acetate). Thus, a mixture comprising limonene-4-ol of the formula (I), terpinene-4-ol of the formula (II) and the at least one inert organic solvent selected from carboxylic acid esters (preferably any one of the preferred carboxylic acid esters as described herein, in particular ethyl acetate) is obtained from the aforementioned isomerization and/or hydrogenation procedures.

The process according to the present invention is carried out in the presence of at least one nickel catalyst.

The term "nickel catalyst" as used herein refers to a catalyst comprising nickel including, for example and without limitation, zero valent nickel, nickel in an ionic form, and nickel in an alloy. The nickel catalyst may be any nickel-containing catalyst suitable for hydrogenation reactions.

For example, nickel catalysts useful in the present invention include but are not limited to the following materials:
(1) relatively pure metallic nickel that may be in finely subdivided form;
(2) metallic nickel further modified with small amounts of other metals such as cobalt, chromium and zirconium; and
(3) metallic nickel in pure form or modified with small amounts of other metals supported on an inert carrier such as kieselguhr, charcoal, clays, alumina, etc.

Preferably, the nickel catalyst is Raney nickel.

Raney nickel is a well-known and commercially available hydrogenation catalyst which was described originally in U.S. Pat. No. 1,638,190. Raney nickel may be prepared by alloying nickel and aluminum and leaching out the aluminum with alkali to expose nickel as a finely divided porous solid in which form nickel is an effective hydrogenation catalyst.

Since Raney nickel is highly pyrophoric when dry, it is typically supplied as a 50% slurry in water. Thus, a certain amount of water may still be present in the Raney nickel catalyst at the time of its application.

In another embodiment, an anhydrous (or substantially anhydrous) Raney nickel catalyst is used in the present invention. The anhydrous (or substantially anhydrous) Raney nickel catalyst may be prepared by washing the moist Raney nickel paste with a solvent selected from ethanol, ethyl acetate or a combination of both. Preferably, the anhydrous (or substantially anhydrous) Raney nickel catalyst is prepared by first washing the moist Raney nickel paste with ethanol and subsequent washing with ethyl acetate. In this regard, the term "substantially anhydrous" as used herein means that trace amounts of water contained in the Raney nickel catalyst can be tolerated.

The molar ratio of the nickel catalyst to limonene-4-ol (I) can vary and depends on the form and composition of the nickel catalyst and the reaction conditions used, but is generally from 0.01:1 to 0.5:1, preferably from 0.05:1 to 0.3:1 and more preferably from 0.1:1 to 0.2:1.

The inert organic solvent used in the process of this invention is selected from carboxylic acid esters. By "inert organic solvent" is meant an organic solvent which, under the reaction conditions of the process of this invention, does not enter into any appreciable reaction with either the reactants or the products.

In a preferred embodiment of the present invention, the carboxylic acid ester is selected from esters of the general formula $R^1COOR^2$ wherein $R^1$ is hydrogen or a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl and $R^2$ is a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl, each of the aforementioned groups optionally being substituted with one or more substituents selected from $C_1$-$C_4$-alkoxy.

The organic moieties mentioned in the definition of the variables $R^1$ and $R^2$ and their substituents are collective terms for individual enumerations of the individual group members. All hydrocarbon chains, e.g. alkyl chains, can be straight-chain or branched, the prefix $C_n$-$C_m$ denoting in each case the possible number of carbon atoms in the group.

Examples of such radicals are:
$C_1$-$C_4$-alkyl: for example methyl, ethyl, n-propyl, isopropyl, n-butyl, 2-butyl (sec-butyl), isobutyl and tert-butyl;
$C_3$-$C_6$-cycloalkyl: monocyclic saturated hydrocarbon group having 3 to 6 ring members, such as cyclopropyl, cyclobutyl, cyclopentyl and cyclohexyl;

$C_1$-$C_4$-alkoxy, for example, methoxy, ethoxy, propoxy, butoxy, 1-methylpropoxy, 2-methylpropoxy and 1,1-dimethylethoxy;

$C_6$-$C_{10}$-aryl: aromatic mono- or bi-cyclic ring having 6 to 10 carbon atoms, for example phenyl, naphthyl and the like;

$C_6$-$C_{10}$-aryl-$C_1$-$C_4$-alkyl: a $C_6$-$C_{10}$-aryl substituent as defined herein that is linked to the carbon atom of the carboxylic acid moiety by a saturated alkyl group having from one to four carbon atoms, e.g. phenyl-$(CH_2)_2$—.

More preferably, the carboxylic acid ester is selected from esters of the general formula $R^1COOR^2$ wherein $R^1$ is hydrogen or $C_1$-$C_4$-alkyl and $R^2$ is a group selected from $C_1$-$C_4$-alkyl, $C_3$-$C_6$-cycloalkyl, $C_6$-$C_{10}$-aryl and $C_6$-$C_{10}$-aryl-$C_1$-$C_4$-alkyl.

Still more preferably, the carboxylic acid ester is selected from esters of the general formula $R^1COOR^2$ wherein $R^1$ is hydrogen or $C_1$-$C_4$-alkyl and $R^2$ is $C_1$-$C_4$-alkyl or $C_3$-$C_6$-cycloalkyl.

Even more preferably, the carboxylic acid ester is selected from esters of the general formula $R^1COOR^2$ wherein $R^1$ is hydrogen or $C_1$-$C_4$-alkyl and $R^2$ is $C_1$-$C_4$-alkyl.

Yet even more preferably, the carboxylic acid ester is selected from esters of the general formula $R^1COOR^2$ wherein $R^1$ and $R^2$ are $C_1$-$C_4$-alkyl.

In another embodiment, the carboxylic acid ester is selected from methyl formate, ethyl formate, n-propyl formate, iso-propyl formate, n-butyl formate, iso-butyl formate, sec-butyl formate, tert-butyl formate, methyl acetate, ethyl acetate, n-propyl acetate, iso-propyl acetate, n-butyl acetate, iso-butyl acetate, sec-butyl acetate, tert-butyl acetate, n-propyl propionate, methyl butyrate, ethyl butyrate, n-butyl n-butyrate, cyclohexyl acetate, and any mixture thereof.

Preferably, the carboxylic acid ester is selected from $C_1$-$C_4$-alkyl acetates, in particular a $C_1$-$C_4$-alkyl acetate selected from ethyl acetate, n-propyl acetate, n-butyl acetate, and any mixture thereof. Particular preference is given to ethyl acetate.

The carboxylic acid ester is usually used in excess relative to limonene-4-ol (I) used as the starting material. The molar ratio of the carboxylic acid ester (preferably the $C_1$-$C_4$-alkyl acetate, in particular ethyl acetate) to limonene-4-ol (I) is generally from 0.5:1 to 10:1, preferably from 1:1 to 5:1 and more preferably from 1.5:1 to 3.5:1.

According to the process of this invention, limonene-4-ol (I) is contacted with hydrogen in the presence of at least one nickel catalyst and at least one inert organic solvent selected from carboxylic acid esters.

It is expedient to carry out the process of this invention at a hydrogen overpressure. The hydrogen overpressure used in the present invention can vary widely and is usually from 5 mbar to 8 bar, preferably from 10 mbar to 6 bar, more preferably from 50 mbar to 6 bar, even more preferably from 10 mbar to 3 bar and yet more preferably from 100 mbar to 3 bar.

Optionally, an inert gas can be used in combination with hydrogen, especially for excluding oxygen from the reaction medium. Suitable inert gases include but are not limited to nitrogen.

The temperature used in the present invention can also vary widely and is usually from 0 to 75° C., preferably from 20 to 70° C., more preferably from 30 to 70° C., even more preferably from 35 to 70° C. and yet more preferably from 40 to 60° C.

In a particularly preferred embodiment of the process of this invention, the hydrogen overpressure is from 10 mbar to 3 bar and the temperature is from 35 to 70° C.

In an especially preferred embodiment, the hydrogen overpressure is from 100 mbar to 3 bar and the temperature is from 40 to 60° C.

The reaction time can vary in a wide range and depends on a variety of factors such as, for example, temperature, pressure, or the equipment used. Typical reaction times are in the range of from 1 to 15 hours, preferably 1 to 6 hours and more preferably 1 to 3 hours.

The process of this invention may be conducted in a batchwise or continuous manner. The reactor used can be a stirred tank reactor, packed column or a combination thereof.

In the batch process, limonene-4-ol (I), the inert organic solvent selected from carboxylic acid esters (preferably ethyl acetate) and the nickel catalyst (preferably Raney nickel) may be combined in a suitable reactor to form a reaction mixture, and the reaction mixture is held at a suitable temperature and hydrogen pressure (normally under agitation) until a desired degree of conversion is obtained.

In the continuous mode, a mixture of limonene-4-ol (I) and the inert organic solvent selected from carboxylic acid esters (preferably ethyl acetate) may be passed through or over a bed or body of the nickel catalyst, preferably Raney nickel (which may be under agitation), at a suitable temperature and hydrogen pressure to form a product stream, and the desired product may be recovered from the stream by conventional methods such as fractional distillation.

In one embodiment of the present invention, limonene-4-ol (I) and the inert organic solvent selected from carboxylic acid esters (preferably ethyl acetate) are charged into a reactor under inert gas atmosphere (preferably nitrogen atmosphere) to give a first mixture, the nickel catalyst (preferably Raney nickel) is added to the first mixture to give a second mixture, and the second mixture is held at a suitable temperature and hydrogen pressure (normally under agitation) to give terpinene-4-ol (II). Preferably, limonene-4-ol (I) is dissolved in the inert organic solvent selected from carboxylic acid esters (preferably ethyl acetate). Thus, in a preferred embodiment, a solution of limonene-4-ol (I) in the inert organic solvent selected from carboxylic acid esters (preferably ethyl acetate) is charged into a reactor under inert gas atmosphere (preferably nitrogen atmosphere), the nickel catalyst (preferably Raney nickel) is added to said solution to give a mixture and said mixture is held at a suitable temperature and hydrogen pressure (normally under agitation) to give terpinene-4-ol (II). For example, the concentration of limonene-4-ol (I) in the aforementioned solution is from 50 to 10% by weight, preferably 50 to 25% by weight relative to the total weight of the solution.

In another embodiment of the present invention, limonene-4-ol (I), the inert organic solvent selected from carboxylic acid esters (preferably ethyl acetate) and the nickel catalyst (preferably Raney nickel) are charged into a reactor under inert gas atmosphere (preferably nitrogen atmosphere) to give a mixture, and said mixture is held at a suitable temperature and hydrogen pressure (normally under agitation) to give terpinene-4-ol (II).

In yet another embodiment of the present invention, the inert organic solvent selected from carboxylic acid esters (preferably ethyl acetate) and the nickel catalyst (preferably Raney nickel) are charged into a reactor under inert gas atmosphere (preferably nitrogen atmosphere) to give a first mixture, limonene-4-ol (I) is added to the first mixture to give a second mixture, and the second mixture is held at a suitable temperature and hydrogen pressure (normally under agitation) to give terpinene-4-ol (II).

Terpinene-4-ol (II) can be isolated from the final reaction mixture by using conventional separation methods such as, for example, distillation.

In a preferred embodiment, the nickel catalyst is removed from the final reaction mixture, for example by conventional separation methods, preferably by filtration.

More preferably, the nickel catalyst and the carboxylic acid ester are both removed from the final reaction mixture, for example by using conventional separation methods (e.g. by filtration, distillation, solvent extraction, or the like).

In an even more preferred embodiment, the nickel catalyst is removed from the final reaction mixture (preferably by filtration) and the carboxylic acid ester is subsequently removed from the mixture obtained from the step of removing the nickel catalyst (e.g. preferably by distillation at reduced pressure).

In particular, the nickel catalyst is filtered off from the final reaction mixture to give a filtrate, and the carboxylic acid ester is subsequently removed from the filtrate, preferably by distillation at reduced pressure.

The aforementioned work-up procedures may already provide terpinene-4-ol (II) in relatively high purity. If necessary, terpinene-4-ol (II) can be subjected to conventional purification steps. For example, terpinene-4-ol (II) may be purified by rectification under reduced pressure.

Terpinene-4-ol (II) (either in pure form or contained in a mixture obtained from any one of the aforementioned work-up procedures) may also be used in one or more subsequent reaction steps. For example, terpinene-4-ol (II) may be used as a starting material for the synthesis of oxabicycloalkane herbicides, in particular of (±)-2-exo-(2-Methylbenzyloxy)-1-methyl-4-isopropyl-7-oxabicyclo[2.2.1]heptane as described, for example in U.S. Pat. No. 4,487,945 or U.S. Pat. No. 4,542,244.

(±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

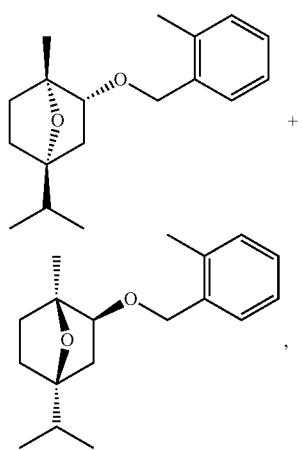

is the racemic mixture containing equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1). The exo-(±)-isomers, the exo-(+)-isomer and the exo-(−)-isomer including their preparation and herbicidal properties are disclosed in EP 0 081 893 A2 (see Examples 29, 34, 35 and 62). Further preparation methods of these compounds are described in U.S. Pat. No. 4,487,945 (see Embodiments 46 and 48). The racemic mixture (±)-2-exo-(2-Methylbenzyloxy)-1-methyl-4-isopropyl-7-oxabicyclo[2.2.1]heptane is also described in the The Pesticide Manual, Fourteenth Edition, Editor: C. D. S. Tomlin, British Crop Production Council, 2006, entry 157, pages 195-196 with its common name cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane.

Terpinene-4-ol (II) is a valuable intermediate in the preparation of (±)-2-exo-(2-Methylbenzyloxy)-1-methyl-4-isopropyl-7-oxabicyclo[2.2.1]heptane, any of its individual enantiomers or any non-racemic mixture thereof.

Terpinene-4-ol (II) may be further converted into (±)-2-exo-(2-Methylbenzyloxy)-1-methyl-4-isopropyl-7-oxabicyclo[2.2.1]heptane, any of its individual enantiomers or any non-racemic mixture thereof. Further conversion into (±)-2-exo-(2-Methylbenzyloxy)-1-methyl-4-isopropyl-7-oxabicyclo[2.2.1]heptane, any of its individual enantiomers or any non-racemic mixture thereof can be accomplished by methods known in the art such as, for example, those described in EP 0 081 893 A2 and U.S. Pat. No. 4,487,945.

Thus, in a further aspect of the present invention, there is provided a process for preparing (±)-2-exo-(2-Methylbenzyloxy)-1-methyl-4-isopropyl-7-oxabicyclo[2.2.1]heptane, any of its individual enantiomers or any non-racemic mixture thereof comprising the steps of:
(i) preparing terpinene-4-ol of formula (II) as described herein, and
(ii) converting terpinene-4-ol of formula (II) into (±)-2-exo-(2-Methylbenzyloxy)-1-methyl-4-isopropyl-7-oxabicyclo[2.2.1]heptane, any of its individual enantiomers or any non-racemic mixture thereof.

The invention is illustrated by the following examples without being limited thereto or thereby.

EXAMPLE 1

6 g (0.102 mol) Raney-nickel (previously washed with ethanol and ethyl acetate) and 71 g ethyl acetate were placed in the reaction vessel. 318.7 g of a solution containing 27.93 w/w % limonene-4-ol (0.5848 mol) and 6.07 w/w % terpinene-4-ol (0.1254 mol) in ethyl acetate were added. The reactor was purged with nitrogen and hydrogen (very slow stirring). Then reaction mixture was pressurized with 100 mbar $H_2$ under vigorous stirring and heated to 50° C. The temperature of the reaction mixture was held between 50° C. and 58° C. with cooling. Hydrogen adsorption was competed after 2 h. Then reaction mixture was cooled to 25° C. and the pressure was released. The catalyst was filtered off through a layer of diatomaceous earth. The remaining catalyst was washed with ethyl acetate. Filtrate and wash ethyl acetate were combined and ethyl acetate was distilled off at reduced pressure (distillation residue: 145.8 g). Quantitative gas chromatography (GC) (GC with internal standard) of the distillation residue showed a terpinene-4-ol concentration of 69.2% and 0% for limonene-4-ol. This corresponds to a yield of 90.4% for terpinene-4-ol (referred to the limonene-4-ol in the starting mixture, without the pre-existing terpinene-4-ol). Additional terpinene-4-ol was found in the distillate (1.35% yield). The total yield for terpinene-4-ol (referred to the limonene-4-ol in the starting mixture, without the pre-existing terpinene-4-ol) was 91.95%.

EXAMPLE 2

Another hydrogenation experiment was performed under the same reaction conditions as in Example 1 but starting with 629.9 g of a solution containing 11.81 w/w % limonene-4-ol (0.4888 mol) and 2.53 w/w % terpinene-4-ol (0.1033 mol). 113.7 g of distillation residue were obtained. Quantitative GC (GC with internal standard) of the distillation residue showed a terpinene-4-ol concentration of 75.24% and 0% for limonene-4-ol. This corresponds to a yield of 93.85% for terpinene-4-ol (referred to the limonene-4-ol in the starting mixture, without the pre-existing terpinene-4-ol).

EXAMPLE 3

16.7 g Raney-nickel (water wet, 34% water; 0.188 mol) were purged in the reaction vessel with 5 g of water. 1297 g of a solution containing 32.0 w/w % limonene-4-ol (2.728 mol) and 7.1 w/w % terpinene-4-ol (0.60 mol) in ethyl acetate were added. The reactor was purged with nitrogen and hydrogen (very slow stirring). Then reaction mixture was pressurized with 100 mbar $H_2$ under vigorous stirring and heated to 50° C. The temperature of the reaction mixture was held at 50° C. with cooling. Hydrogen adsorption was completed after 5 h. Then reaction mixture was cooled to 25° C. and the pressure was released. The catalyst was filtered off through a filter cloth. The remaining catalyst was washed with ethyl acetate. Filtrate and wash ethyl acetate were combined and ethyl acetate was distilled off at reduced pressure (distillation residue: 854.6 g). Quantitative gas chromatography (GC) (GC with internal standard) of the distillation residue showed a terpinene-4-ol concentration of 58.5% and 0% for limonene-4-ol. This corresponds to a yield of 96.76% for terpinene-4-ol (referred to the limonene-4-ol in the starting mixture, without the pre-existing terpinene-4-ol). Additional terpinene-4-ol was found in the distillate (1.04% yield). The total yield for terpinene-4-ol (referred to the limonene-4-ol in the starting mixture, without the pre-existing terpinene-4-ol) was 97.8%.

COMPARATIVE EXAMPLE 1

16.7 g Raney-nickel (water wet, 34% water; 0.188 mol) were purged in the reaction vessel with 5 g of water. 1297 g of a solution containing 31.8 w/w % limonene-4-ol (2.712 mol) and 7.0 w/w % terpinene-4-ol (0.59 mol) in ethanol were added. The reactor was purged with nitrogen and hydrogen (very slow stirring). Then reaction mixture was pressurized with 100 mbar $H_2$ under vigorous stirring and heated to 50° C. The temperature of the reaction mixture was held at 50° C. with cooling. Hydrogen adsorption was completed after 7.5 h. Then reaction mixture was cooled to 25° C. and the pressure was released. The catalyst was filtered off through a filter cloth. The remaining catalyst was washed with ethanol. Filtrate and wash ethanol were combined and ethanol was distilled off at reduced pressure (distillation residue: 802.5 g). Quantitative gas chromatography (GC) (GC with internal standard) of the distillation residue showed a terpinene-4-ol concentration of 59.5% and 0% for limonene-4-ol. This corresponds to a yield of 92.41% for terpinene-4-ol (referred to the limonene-4-ol in the starting mixture, without the pre-existing terpinene-4-ol). Additional terpinene-4-ol was found in the distillate (3.05% yield). The total yield for terpinene-4-ol (referred to the limonene-4-ol in the starting mixture, without the pre-existing terpinene-4-ol) was 95.46%.

The results of Example 3 and Comparative Example 1 demonstrate that the use of a carboxylic acid ester (i.e. ethyl acetate) as reaction solvent according to this invention gives a higher yield of terpinene-4-ol at a shorter reaction time (yield: 97.8%, reaction time: 5 h) as compared to the known use of ethanol (yield: 95.46%, reaction time: 7.5 h). The improvement of 2.34% in the yield at an even shorter reaction time is significant in view of the fact that the process of this invention is intended for the production of terpinene-4-ol on a large industrial scale.

The invention claimed is:

1. A process for preparing terpinene-4-ol of formula (II)

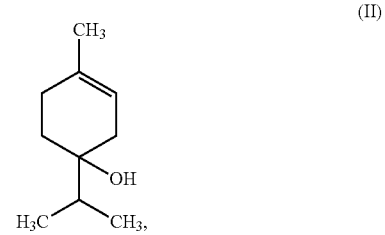

(II)

said process comprising contacting limonene-4-ol of formula (I)

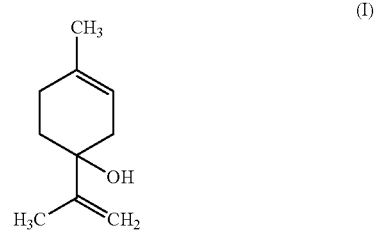

(I)

with hydrogen in the presence of at least one nickel catalyst and at least one inert organic solvent selected from carboxylic acid esters.

2. The process of claim 1, wherein the nickel catalyst comprises Raney nickel.

3. The process of claim 1, wherein the carboxylic acid ester is selected from esters of the general formula $R^1COOR^2$ wherein $R^1$ is hydrogen or selected from the group consisting of $C_1$-$C_4$-alkyl, $C_3$-$C_6$-cycloalkyl, $C_6$-$C_{10}$-aryl and $C_6$-$C_{10}$-aryl-$C_1$-$C_4$-alkyl and $R^2$ is selected from the group consisting of $C_1$-$C_4$-alkyl, $C_3$-$C_6$-cycloalkyl, $C_6$-$C_{10}$-aryl and $C_6$-$C_{10}$-aryl-$C_1$-$C_4$-alkyl, each of the aforementioned groups optionally being substituted with one or more substituents selected from $C_1$-$C_4$-alkoxy.

4. The process of claim 1, wherein the carboxylic acid ester is selected from $C_1$-$C_4$-alkyl acetates.

5. The process of claim 1, wherein the carboxylic acid ester is ethyl acetate.

6. The process of claim 1, wherein the temperature is from 35 to 70° C.

7. The process of claim 1, wherein the hydrogen overpressure is from 10 mbar to 3 bar.

8. The process of claim 1, wherein limonene-4-ol of formula (I) is prepared by isomerization of terpinolene epoxide of the formula (III)

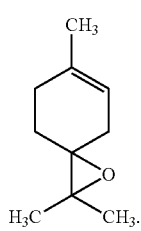

(III)

9. The process of claim 8, wherein terpinolene epoxide of the formula (III) is further subjected to hydrogenation.

10. The process of claim 8, wherein the isomerization and/or hydrogenation are carried out in the presence of at least one copper catalyst.

11. The process claim 8, wherein the isomerization and/or hydrogenation are carried out in the presence of at least one inert organic solvent selected from carboxylic acid esters.

12. The process of claim 11, wherein a mixture comprising limonene-4-ol of the formula (I), terpinene-4-ol of the formula (II) and the at least one inert organic solvent selected from carboxylic acid esters is obtained.

13. The process of claim 1, wherein terpinene-4-ol of the formula (II) is further converted into (±)-2-exo-(2-Methylbenzyloxy)-1-methyl-4-isopropyl-7-oxabicyclo[2.2.1]heptane, any of its individual enantiomers or any non-racemic mixture thereof.

* * * * *